(12) United States Patent
Mower

(10) Patent No.: US 6,295,470 B1
(45) Date of Patent: Sep. 25, 2001

(54) ANTITACHYCARDIAL PACING

(75) Inventor: Morton M. Mower, Baltimore, MD (US)

(73) Assignee: The Mower Family CHF Treatment Irrevocable Trust, Baltimore, MD (US)

(*) Notice: Subject to any disclaimer, the term of this patent is extended or adjusted under 35 U.S.C. 154(b) by 0 days.

(21) Appl. No.: 09/231,570

(22) Filed: Jan. 14, 1999

Related U.S. Application Data

(63) Continuation-in-part of application No. 08/699,552, filed on Aug. 19, 1996, now Pat. No. 5,871,506.

(51) Int. Cl.$^7$ ................................................ A61N 1/362
(52) U.S. Cl. .................................................. 607/14; 607/5
(58) Field of Search ........................... 607/4, 5, 14, 28

(56) References Cited

U.S. PATENT DOCUMENTS

| | | | |
|---|---|---|---|
| 3,924,641 | 12/1975 | Weiss | 128/419 |
| 3,946,745 | 3/1976 | Hsiang-Lai et al. | 128/421 |
| 4,010,758 | 3/1977 | Rockland et al. | 128/418 |
| 4,343,312 | 8/1982 | Cals et al. | 128/419 |
| 4,402,322 | 9/1983 | Duggan | 128/419 |
| 4,481,953 | 11/1984 | Gold et al. | 128/786 |
| 4,498,478 | 2/1985 | Bourgeois | 128/419 |
| 4,545,956 | 10/1985 | Herscovoci | 128/419 |
| 4,662,377 | 5/1987 | Heilman et al. | 128/419 D |
| 4,729,376 | 3/1988 | DeCote, Jr. | 128/419 |
| 4,903,700 | 2/1990 | Whigham et al. | 128/419 |
| 5,083,564 | 1/1992 | Scherlag | 128/419 PG |
| 5,105,810 | 4/1992 | Collins et al. | 128/419 D |
| 5,209,229 * | 5/1993 | Gilli . | |
| 5,233,985 | 8/1993 | Hudrlik | 607/27 |
| 5,318,591 | 6/1994 | Causey, III et al. | 607/5 |
| 5,417,718 | 5/1995 | Kleks et al. | 607/28 |
| 5,458,619 | 10/1995 | Olson | 607/4 |
| 5,480,413 | 1/1996 | Greenhut et al. | 607/14 |
| 5,534,015 | 7/1996 | Kroll et al. | 607/7 |
| 5,549,652 | 8/1996 | McClure et al. | 607/28 |
| 5,601,608 | 2/1997 | Mouchawar | 607/5 |
| 5,601,615 | 2/1997 | Markowitz et al. | 607/28 |
| 5,649,966 | 7/1997 | Noren et al. | 607/4 |
| 5,658,319 | 8/1997 | Kroll | 607/7 |
| 5,674,253 | 10/1997 | Adams et al. | 607/7 |
| 5,683,431 | 11/1997 | Wang | 607/28 |
| 5,697,953 | 12/1997 | Kroll et al. | 607/5 |
| 5,713,924 | 2/1998 | Min et al. | 607/4 |
| 5,713,929 | 2/1998 | Hess et al. | 607/14 |
| 5,718,720 | 2/1998 | Prutchi et al. | 607/28 |
| 5,814,079 | 9/1998 | Kieval | 607/4 |
| 5,871,506 | 2/1999 | Mower | 607/9 |

FOREIGN PATENT DOCUMENTS

| | | | |
|---|---|---|---|
| 0491649 A2 | 6/1992 | (EP) | A61N/1/39 |
| 0600631 A2 | 11/1993 | (EP) | A61N/1/368 |
| 0813889 A2 | 12/1997 | (EP) | A61N/1/368 |
| 0 870 516 A2 | 10/1998 | (EP) . | |
| 2763247 | 5/1997 | (FR) | A61N/1/365 |
| 93/01861 | 2/1993 | (WO) | A61N/1/36 |
| 97/25098 | 7/1997 | (WO) | A61N/1/00 |
| 99/36124 | 7/1999 | (WO) . | |
| 99/61101 | 12/1999 | (WO) . | |
| 00/01443 | 1/2000 | (WO) . | |

* cited by examiner

*Primary Examiner*—Scott M. Getzow
(74) *Attorney, Agent, or Firm*—Roberts Abokhair & Mardula, LLC

(57) ABSTRACT

Protocols for antitachycardial pacing including biphasic stimulation administered at, or just above, the diastolic depolarization threshold potential; biphasic or conventional stimulation initiated at, or just above, the diastolic depolarization threshold potential, reduced, upon capture, to below threshold; and biphasic or conventional stimulation administered at a level set just below the diastolic depolarization threshold potential. These protocols result in reliable cardiac capture with a lower stimulation level, thereby causing less damage to the heart, extending battery life, causing less pain to the patient and having greater therapeutic effectiveness. In those protocols using biphasic cardiac pacing, a first and second stimulation phase is administered. The first stimulation phase has a predefined polarity, amplitude and duration. The second stimulation phase also has a predefined polarity, amplitude and duration. The two phases are applied sequentially. Contrary to current thought, anodal stimulation is first applied and followed by cathodal stimulation. In this fashion, pulse conduction through the cardiac muscle is improved together with the increase in contractility.

62 Claims, 7 Drawing Sheets

ANTITACHYCARDIAL PACING

RELATED APPLICATION DATA

The present disclosure is a continuation-in-part application related to the U.S. patent application entitled "Augmentation of Electrical Conduction and Contractility by Biphasic Cardiac Pacing", Ser. No. 08/699,552, filed Aug. 19, 1996, now U.S. Pat. No. 5,871,506.

FIELD OF THE INVENTION

The present invention relates generally to implantable cardioverter/defibrillator with antitachycardial pacing capabilities and/or a method of such pacing.

BACKGROUND OF THE INVENTION

The typical implantable cardioverter/defibrillator (ICD) delivers an initial electrical countershock within ten to twenty seconds of arrhythmia onset, thereby saving countless lives. Improved devices have antitachycardia pacing capabilities in addition to cardioverting/defibrillating functions. These ICDs are capable of different initial responses to one or more tachycardia as well as a programmable sequence of responses to a particular arrhythmia.

The output energy level is generally set by a physician in accordance with a patient's capture threshold, determined at the time of heart implantation. This threshold represents the minimum pacing energy required to reliably stimulate a patient's heart. However, due to trauma associated with the stimulation, scar tissue grows at the interface between the implanted cardiac pacer leads and the myocardium. This scar tissue boosts the patient's capture threshold. To insure reliable cardiac capture, the output energy level is thus generally set at a level which is a minimum of two times greater than the initially measured capture threshold. A drawback to such an approach is that the higher stimulation level causes more trauma to the cardiac tissue than would a lower level of stimulation, and hence promotes the formation of scar tissue, thereby boosting the capture threshold.

The higher stimulation level also shortens battery life. This is not desirable, as a shorter battery life necessitates more frequent surgery to implant fresh batteries.

Another drawback is the potential for patient discomfort associated with this higher stimulation level. This is because the higher stimulation level can stimulate the phrenic or diaphragmatic plexus or cause intercostal muscle pacing.

Lastly, the higher stimulation is less effective, due to entry block.

A need therefore exists for an ICD that can achieve reliable cardiac capture with a lower stimulation level, thereby causing less damage to the heart, extending battery life, causing less pain to the patient and having greater therapeutic effectiveness than current ICDs. A need also exists for an ICD that can better entrain the heart and can entrain portions of the heart from a greater distance.

SUMMARY OF THE INVENTION

It therefore is an object of the present invention to provide an ICD with antitachycardial pacing capabilities, wherein the stimulation is administered with a voltage either at, just above, or just below the diastolic depolarization threshold potential.

It is another object of the present invention to sense whether cardiac capture has occurred, and if not, to administer additional stimulation.

It is another object of the present invention to provide the additional stimulation at a slightly higher voltage level than that level of stimulation which resulted in no capture.

It is another object of the present invention to repeat the stimulation—sensing cycle until cardiac capture has occurred.

It is another object of the present invention to provide stimulation using a biphasic waveform.

The present invention accomplishes the above objectives by providing an implantable cardioverter-defibrillator with a unique constellation of features and capabilities. Protocols disclosed include:

1/biphasic stimulation administered at, or just above, the diastolic depolarization threshold potential;

2/biphasic or conventional stimulation initiated at, or just above, the diastolic depolarization threshold potential, reduced, upon capture, to below threshold; and 3/biphasic or conventional stimulation administered at a level set just below the diastolic depolarization threshold potential.

As mentioned, the antitachycardial pacing protocols of the present invention can be used in conjunction with biphasic pacing. The method and apparatus relating to biphasic pacing comprises a first and second stimulation phase, with each stimulation phase having a polarity, amplitude, shape, and duration. In a preferred embodiment, the first and second phases have differing polarities. In one alternative embodiment, the two phases are of differing amplitude. In a second alternative embodiment, the two phases are of differing duration. In a third alternative embodiment, the first phase is in a chopped wave form. In a fourth alternative embodiment, the amplitude of the first phase is ramped. In a fifth alternative embodiment the first phase is administered over 200 milliseconds after completion of a cardiac beating/pumping cycle. In a preferred alternative embodiment, the first phase of stimulation is an anodal pulse at maximum subthreshold amplitude for a long duration, and the second phase of stimulation is a cathodal pulse of short duration and high amplitude. It is noted that the aforementioned alternative embodiments can be combined in differing fashions. It is also noted that these alternative embodiments are intended to be presented by way of example only, and are not limiting.

Enhanced myocardial function is obtained through the biphasic pacing of the present invention. The combination of cathodal with anodal pulses of either a stimulating or conditioning nature, preserves the improved conduction and contractility of anodal pacing while eliminating the drawback of increased stimulation threshold. The result is a depolarization wave of increased propagation speed. This increased propagation speed results in superior cardiac contraction leading to an improvement in blood flow and in increased access to reentrant circuits. Improved stimulation at a lower voltage level also results in reduction in scar tissue buildup thereby reducing the tendency of the capture threshold to rise; reduction in power consumption leading to increased life for pacemaker batteries; and decreased pain to the patient.

DESCRIPTION OF THE PREFERRED EMBODIMENTS

Figure 1A:
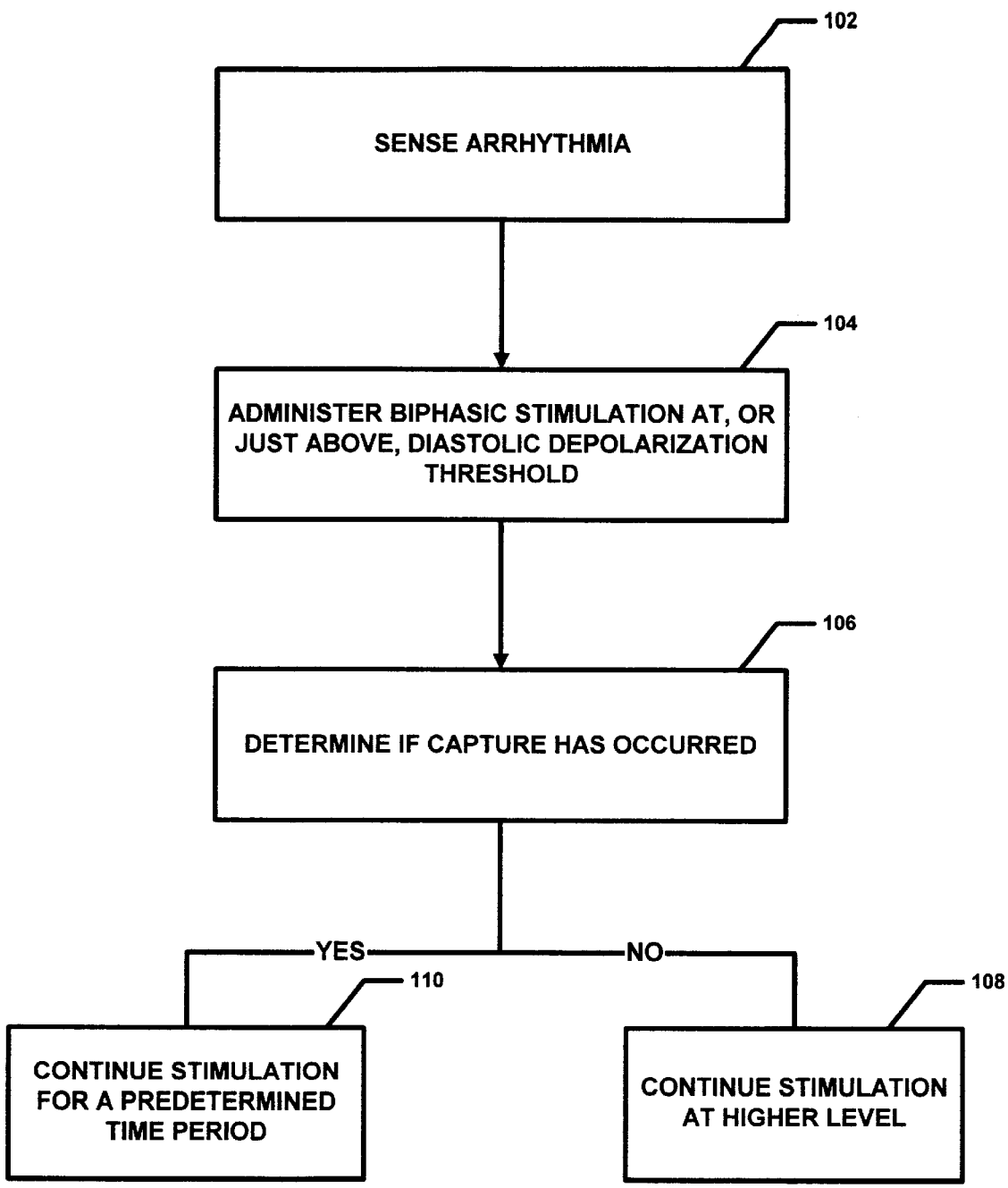
FIGS. 1A–1C illustrate examples of methodologies for treating arrhythmias.
Figure 1B:
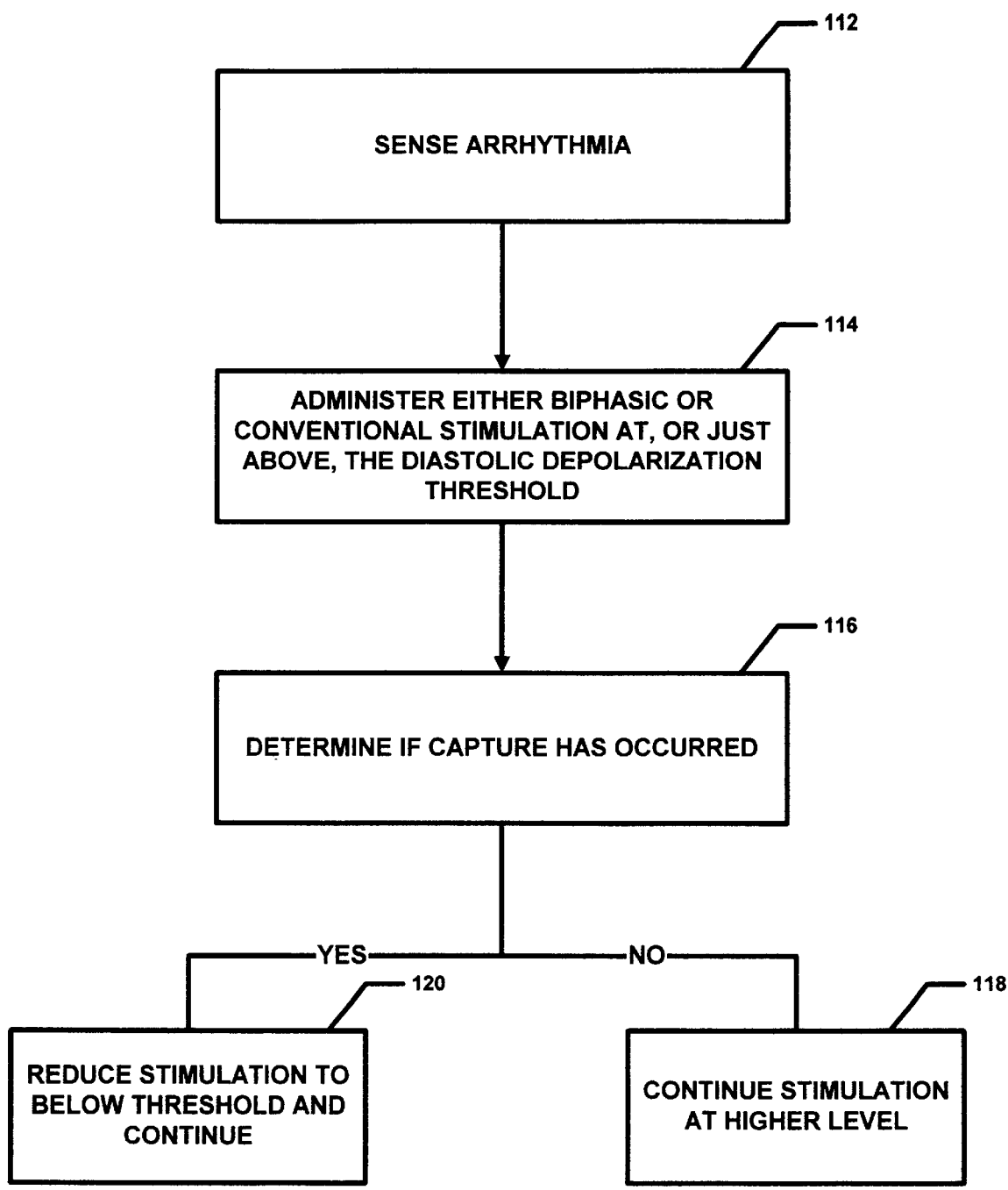
Figure 1C:
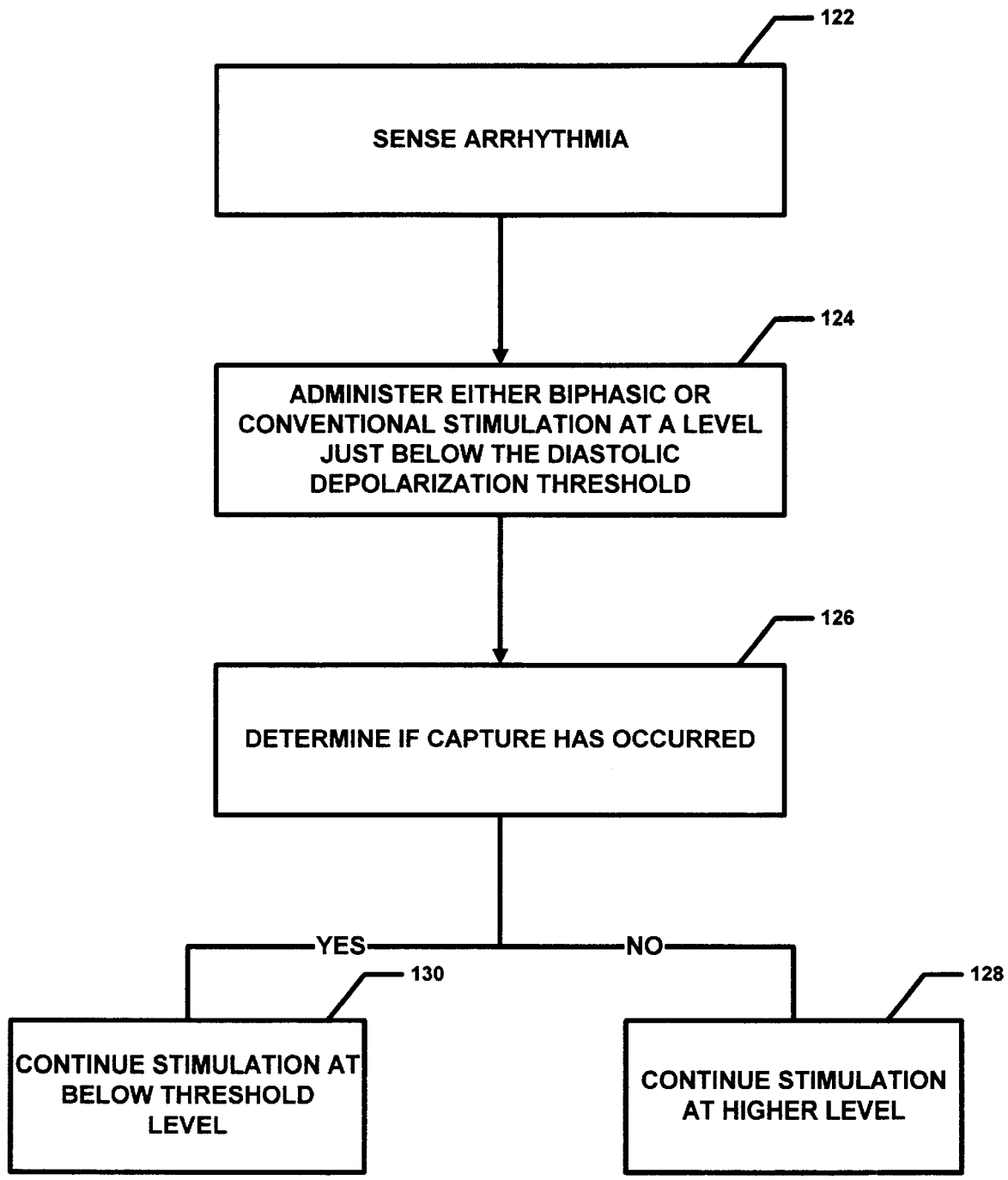

The present invention relates to the use of antitachycardial pacing to break up arrhythmia in the atrium. FIGS. 1A through 1C illustrate examples of methodologies for treating arrhythmias.

FIG. 1A illustrates a first methodology. Here, a sensor senses the onset of arrhythmia 102. In a preferred embodiment, this sensor comprises an antitachycardial pacing algorithm. Biphasic stimulation is then administered 104. In varying embodiments, this stimulation is either at, or just above the diastolic depolarization threshold. The ICD determines whether capture has occurred 106. If capture has not occurred, then stimulation continues at a slightly higher level 108. This stimulation—capture check—boost stimulation cycle continues until capture occurs. If capture has occurred, then stimulation is continued for a predetermined period of time 110. In a preferred embodiment, stimulation is administered as long as the arrhythmia persists.

In a preferred embodiment, stimulation pulses are administered at 80 to 100 percent of the intrinsic rate with an approximately one to two second pause between each set of stimulation pulses. Then either the number of pulses increases, or the timing between pulses is adjusted. For example, in a preferred embodiment, the first pulse sequence can be at 80 percent of the intrinsic heart rate, the second pulse sequence at 82 percent, the third pulse sequence at 84 percent, and so on. In a preferred embodiment a plurality of feedback loops provide data such that the voltage can be adjusted to constantly skirt the capture threshold. Stimulation is continued until the rhythm reverts.

FIG. 1B illustrates a second methodology. Here, a sensor senses the onset of arrhythmia 112. In varying embodiments of the second method, either biphasic or conventional stimulation is then administered 114. This stimulation level is set at or just above the diastolic depolarization threshold potential. The ICD determines whether capture has occurred 116. If capture has not occurred, then stimulation continues at a slightly higher level 118. This stimulation—capture check—boost stimulation cycle continues until capture occurs. If capture has occurred, then stimulation is gradually and continuously reduced to below threshold, and continued 120. Then, if capture is lost, the stimulation is raised to a slightly higher level and is again gradually and continuously reduced. This entire sequence is repeated, such that the stimulation level hovers as close as possible to the lowest stimulation level which provides capture. Stimulation continues until the rhythm reverts, for example, when the antitachycardial pacing algorithm determines that pacing is no longer necessary.

FIG. 1C illustrates a third methodology. Here, a sensor senses the onset of arrhythmia 122. In varying embodiments of the third method, either biphasic or conventional stimulation is then administered 124. This stimulation level is set just below the diastolic depolarization threshold potential. The ICD determines whether capture has occurred 126. If capture has not occurred, then stimulation continues at a slightly higher level 128. This stimulation—capture check—boost stimulation cycle continues until capture occurs. If capture has occurred, then stimulation is continued at below threshold level 130. If capture is lost then the stimulation is raised to a slightly higher level and is gradually and continuously reduced. This entire sequence is repeated, such that the stimulation level hovers as close as possible to the lowest stimulation level which provides capture. Stimulation continues until the rhythm reverts, for example, when the antitachycardial pacing algorithm determines that pacing is no longer necessary.

Sensing

Sensing can be direct or indirect. For example, direct sensing can be based on data from sensing electrodes. The ICD of the present invention includes sensing circuits/electronics to sense an arrhythmia through one or more sensing and/or stimulating electrodes. The sensing electronics sense the cardiac activity as depicted by electrical signals. For example, as is known in the art, R-waves occur upon the depolarization of ventricular tissue and P-waves occur upon the depolarization of atrial tissue. By monitoring these electrical signals the control/timing circuit of the ICD can determine the rate and regularity of the patient's heart beat, and thereby determine whether the heart is undergoing arrhythmia. This determination can be made by determining the rate of the sensed R-waves and/or P-waves and comparing this determined rate against various reference rates.

Direct sensing can be based upon varying criteria; such as, but not limited to, primary rate, sudden onset, and stability. The sole criteria of a primary rate sensor is the heart rate. When applying the primary rate criteria, if the heart rate should exceed a predefined level, then treatment is begun. Sensing electronics set to sudden onset criteria ignore those changes which occur slowly, and initiate treatment when there is a sudden change such as immediate paroxysmal arrhythmia. This type of criteria would thus discriminate against sinus tachycardia. Stability of rate can also be an important criteria. For example, treatment with a ventricular device would not be warranted for a fast rate that varies, here treatment with an atrial device would be indicated.

In alternative embodiments, sensing can be indirect. Indirect sensing can be based on any of various functional parameters such as arterial blood pressure, rate of the electrocardiogram deflections or the probability density function (pdf) of the electrocardiogram. For example, whether or not to administer treatment can also be affected by pdf monitoring of the time the signal spends around the baseline.

Sensing can also be augmented by stimulating the atria and observing and measuring the consequent effects on atrial and ventricular function.

Thus, in a preferred embodiment, sensing electronics are based upon multiple criteria. In addition, the present invention envisions devices working in more than one chamber such that appropriate treatment can be administered to either the atrium or the ventricle in response to sensing electronics based upon a variety of criteria, including those described above as well as other criteria known to those skilled in the art.

Stimulation

Electrical stimulation is delivered via lead(s) or electrode (s). These leads can be epicardial (external surface of the heart) or endocardial (internal surface of the heart) or any combination of epicardial and endocardial. Leads are well known to those skilled in the art; see, for example, U.S. Pat. No. 4,662,377 to Heilman et al., U.S. Pat. No. 4,481,953 to Gold et al., and U.S. Pat. No. 4,010,758 to Rockland et al., each of which is herein incorporated by reference in its entirety.

Figure 2:
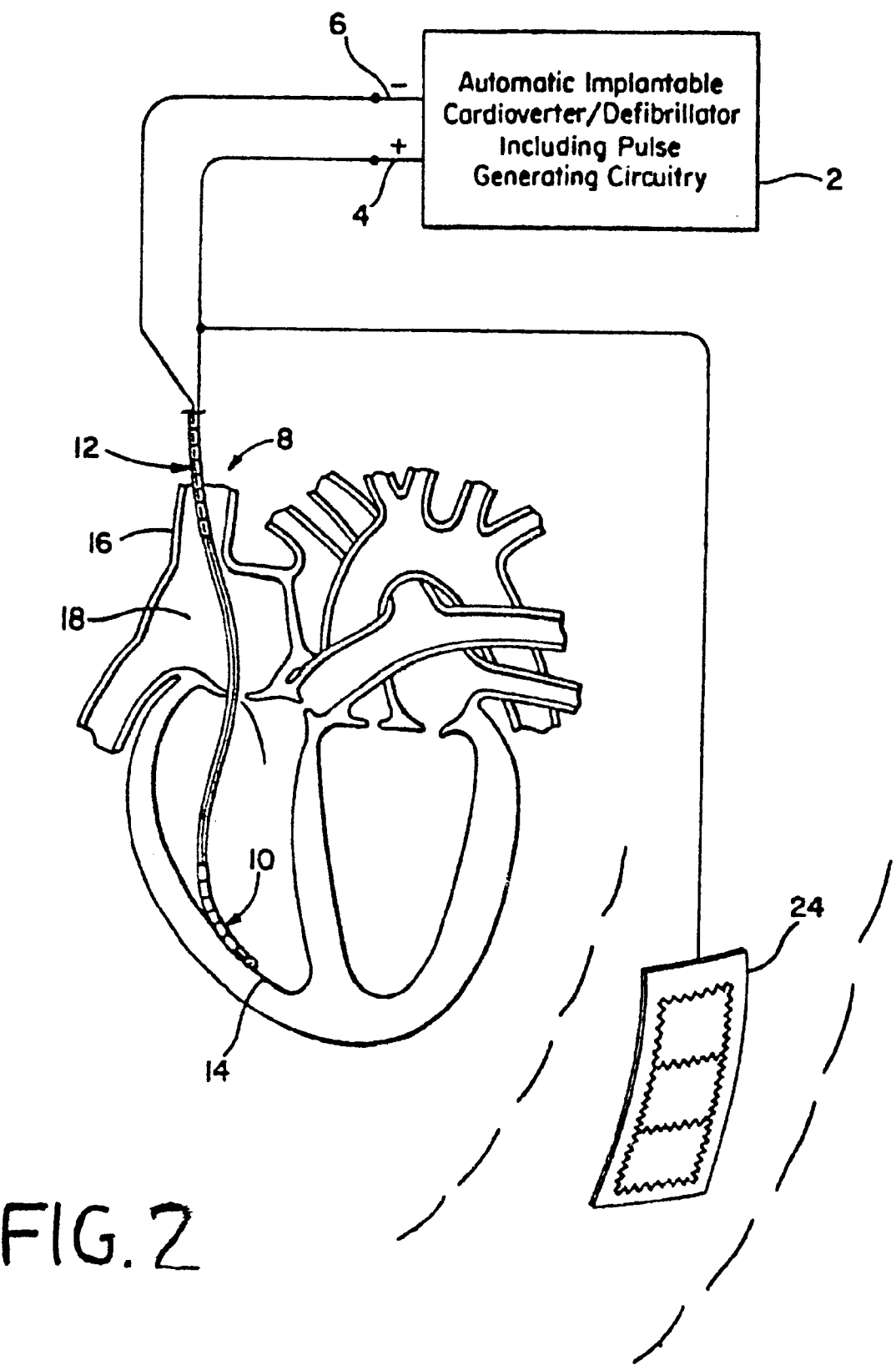
FIG. 2 illustrates an implantable cardioverter/defibrillator according to an embodiment of the present invention.

Lead systems can be unipolar or bipolar. A unipolar lead has one electrode on the lead itself, the cathode. Current flows from the cathode, stimulates the heart, and returns to the anode on the casing of the pulse generator to complete the circuit. A bipolar lead has two poles on the lead a short distance from each other at the distal end, and both electrodes lie within the heart. With the reference to FIG. 2, a system according to an embodiment of the present invention is illustrated. An automatic implantable cardioverter/defibrillator 2 is implanted within the body of the patient and has a pair of output terminals, an anode 4 and a cathode 6. The ICD 2 is coupled to a flexible catheter electrode arrangement 8 having a distal electrode 10 and a proximal electrode 12, each associated with the patient's heart. Other electrode configurations may be employed, such as ring-type electrodes. As for external electrodes, an anodal electrode 24 may be employed. The automatic ICD 2 includes sensing and detecting circuitry, as well as pulse generating circuitry, the output of the latter being coupled to the implantable electrodes 10, 12. The ICD 2 senses an arrhythmic condition of the heart and, in response thereto, issues or emits cardioverting or defibrillating pulses to the heart, through the implantable electrodes 10, 12.

The catheter electrode 8 is inserted intravenously to a position such that the distal electrode 10 is positioned in the right ventricular apex 14 of the heart and the proximal electrode 12 is positioned in the superior vena cava region 16 of the heart. It should be appreciated that, as the term is used herein, the superior vena cava 16 may also include portions of the right atrium 18.

Conventional stimulation is well known to those skilled in the art and comprises monophasic waveforms (cathodal or anodal) as well as multiphasic waveforms wherein the nonstimulating pulses are of a minimal magnitude and are used, for example, to dissipate a residual charge on an electrode.

FIGS. 3 through 7 depict a range of biphasic stimulation protocols. These protocols have been disclosed in U.S. patent application No. 08/699,552 to Mower, which is herein incorporated by reference in its entirety.

Figure 3:
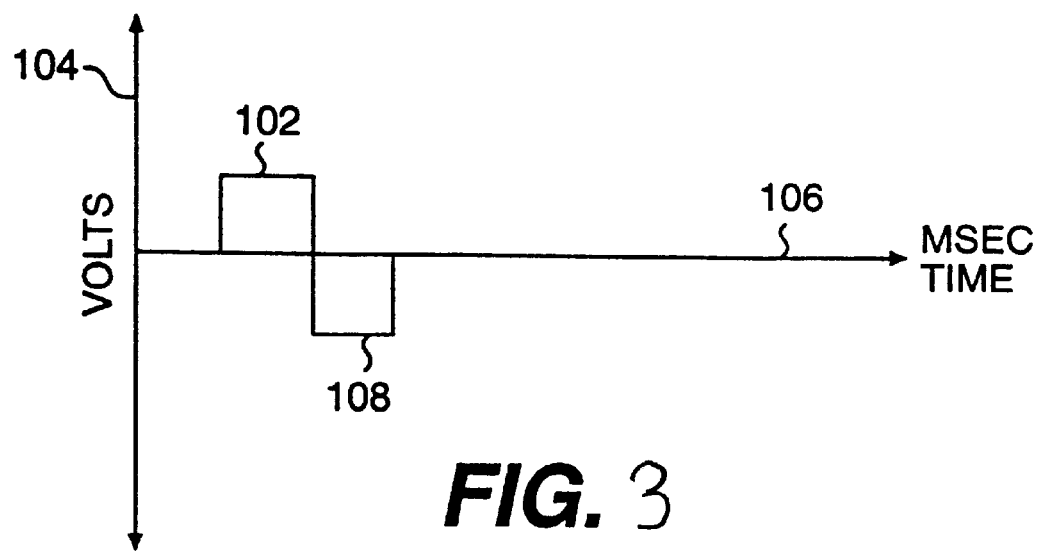
FIG. 3 is a schematic representation of leading anodal biphasic stimulation.

FIG. 3 depicts biphasic electrical stimulation wherein a first stimulation phase comprising anodal stimulus 302 is administered having amplitude 304 and duration 306. This first stimulation phase is immediately followed by a second stimulation phase comprising cathodal stimulation 308 of equal intensity and duration.

Figure 4:
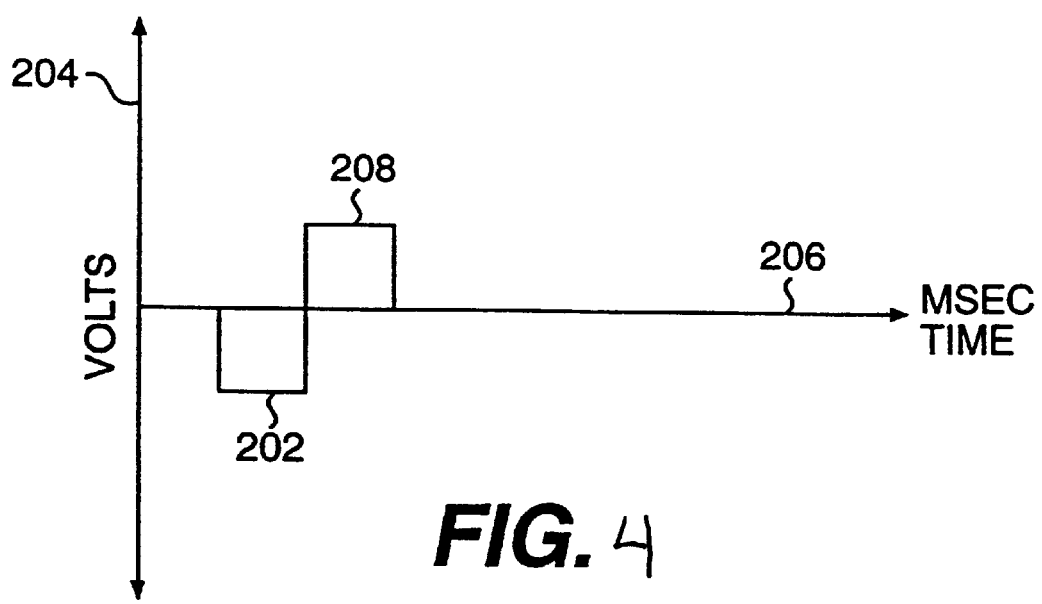
FIG. 4 is a schematic representation of leading cathodal biphasic stimulation.

FIG. 4 depicts biphasic electrical stimulation wherein a first stimulation phase comprising cathodal stimulation 402 having amplitude 404 and duration 406 is administered. This first stimulation phase is immediately followed by a second stimulation phase comprising anodal stimulation 408 of equal intensity and duration.

Figure 5:
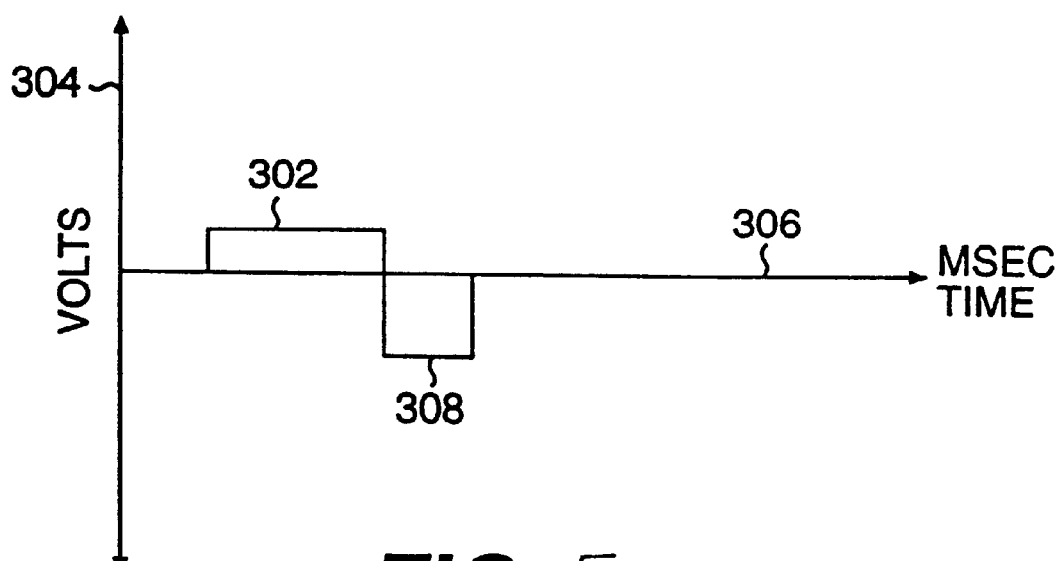
FIG. 5 is a schematic representation of leading anodal stimulation of low level and long duration, followed by conventional cathodal stimulation.

FIG. 5 depicts a preferred embodiment of biphasic stimulation wherein a first stimulation phase, comprising low level, long duration anodal stimulation 502 having amplitude 504 and duration 506, is administered. This first stimulation phase is immediately followed by a second stimulation phase comprising cathodal stimulation 508 of conventional intensity and duration. In differing alternative embodiments, anodal stimulation 502 is: 1) at maximum subthreshold amplitude; 2) less than three volts; 3) of a duration of approximately two to eight milliseconds; and/or 4) administered over 200 milliseconds post heart beat. Maximum subthreshold amplitude is understood to mean the maximum stimulation amplitude that can be administered without eliciting a contraction. In a preferred embodiment, anodal stimulation is approximately two volts for approximately three milliseconds duration. In differing alternative embodiments, cathodal stimulation 508 is: 1) of a short duration; 2) approximately 0.3 to 1.5 milliseconds; 3) of a high amplitude; 4) in the approximate range of three to twenty volts; and/or 5) of a duration less than 0.3 millisecond and at a voltage greater than twenty volts. In a preferred embodiment, cathodal stimulation is approximately six volts administered for approximately 0.4 millisecond. In the manner disclosed by these embodiments, as well as those alterations and modifications which can become obvious upon the reading of this specification, a maximum membrane potential without activation is achieved in the first phase of stimulation.

Figure 6:
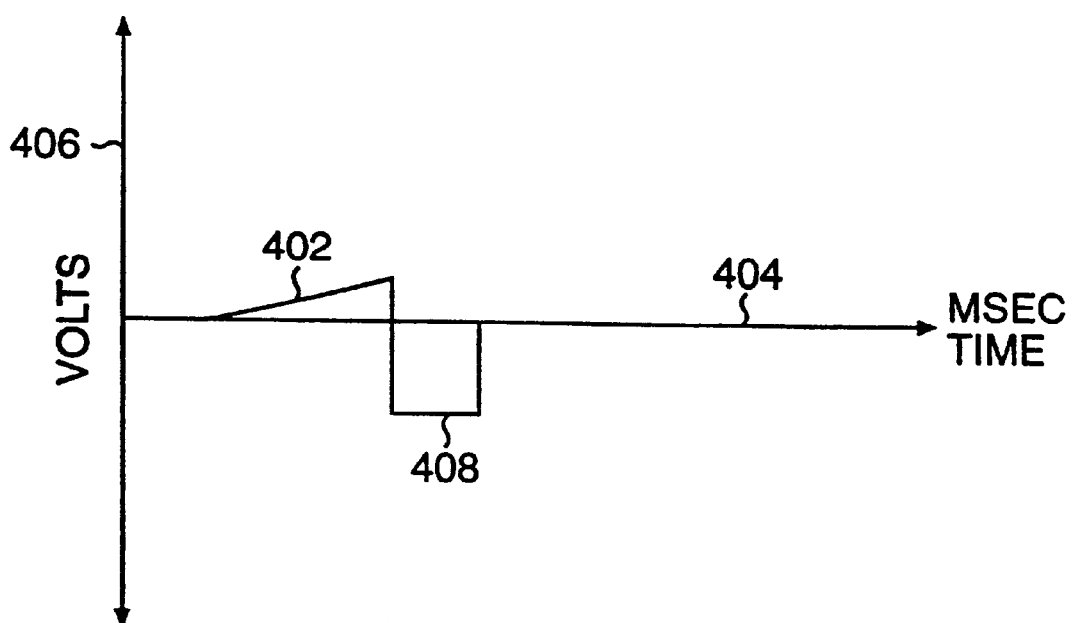
FIG. 6 is a schematic representation of leading anodal stimulation of ramped low level and long duration, followed by conventional cathodal stimulation.

FIG. 6 depicts an alternative preferred embodiment of biphasic stimulation wherein a first stimulation phase, comprising anodal stimulation 602, is administered over period 604 with rising intensity level 606. The ramp of rising intensity level 606 can be linear or non-linear, and the slope can vary. This anodal stimulation is immediately followed by a second stimulation phase comprising cathodal stimulation 608 of conventional intensity and duration. In alternative embodiments, anodal stimulation 602: (1) rises to a maximum subthreshold amplitude less than three volts; (2) is of a duration of approximately two to eight milliseconds; and/or (3) is administered over 200 milliseconds post heart beat. In yet other alternative embodiments, cathodal stimulation 608 is: (1) of a short duration; (2) approximately 0.3 to 1.5 milliseconds; (3) of a high amplitude; (4) in the approximate range of three to twenty volts; and/or (5) of a duration less than 0.3 milliseconds and at a voltage greater than twenty volts. In the manner disclosed by these embodiments, as well as those alterations and modifications which can become obvious upon the reading of this specification, a maximum membrane potential without activation is achieved in the first phase of stimulation.

Figure 7:
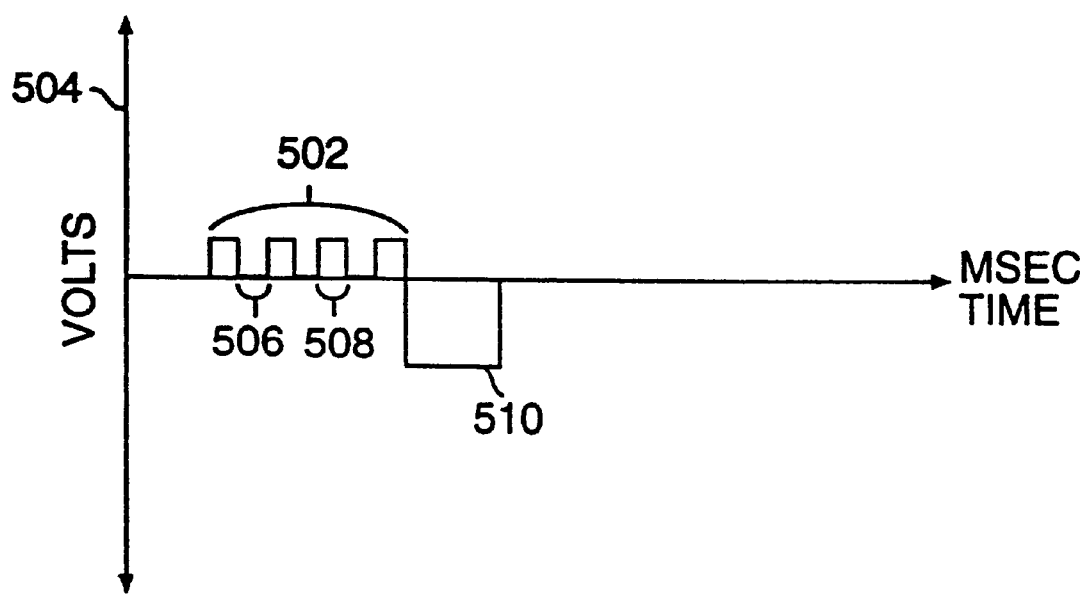
FIG. 7 is a schematic representation of leading anodal stimulation of low level and short duration, administered in series followed by conventional cathodal stimulation.

FIG. 7 depicts biphasic electrical stimulation wherein a first stimulation phase, comprising series 702 of anodal pulses, is administered at amplitude 704. In one embodiment, rest period 706 is of equal duration to stimulation period 708, and is administered at baseline amplitude. In an alternative embodiment, rest period 706 is of a differing duration than stimulation period 708, and is administered at baseline amplitude. Rest period 706 occurs after each stimulation period 708, with the exception that a second stimulation phase, comprising cathodal stimulation 710 of conventional intensity and duration, immediately follows the completion of series 702. In alternative embodiments: (1) the total charge transferred through series 702 of anodal stimulation is at the maximum subthreshold level; and/or (2) the first stimulation pulse of series 702 is administered over 200 milliseconds post heart beat. In yet other alternative embodiments, cathodal stimulation 710 is: (1) of a short duration; (2) approximately 0.3 to 1.5 milliseconds; (3) of a high amplitude; (4) in the approximate range of three to twenty volts, and/or (5) of a duration less than 0.3 milliseconds and at a voltage greater than twenty volts.

Determining Cardiac Capture

Capture can be determined by multiple means. First, capture or the loss thereof, can be determined by monitoring cardiac rhythm. Loss of capture can result in a change in timing of the heart beat.

Second, capture can be monitored through the development of a template. The template can be based on parameters such as electrocardiogram data, mechanical motion and/or probability density function data. Where the template is established pre-stimulation, a change in the baseline signifies capture. Where the template is established after capture has occurred, a change in the template characteristics signifies loss of capture. The templates can be established and/or updated at any time.

Once capture occurs the stimulation protocol of the entrained sites is adjusted as illustrated by FIGS. 1A through 1C.

Having thus described the basic concept of the invention, it will be readily apparent to those skilled in the art that the foregoing detailed disclosure is intended to be presented by way of example only, and is not limiting. Various alterations, improvements and modifications will occur and are intended to those skilled in the art, but are not expressly stated herein. These modifications, alterations and improvements are intended to be suggested hereby, and within the scope of the invention. Further, the pacing pulses described in this specification are well within the capabilities of existing pacemaker electronics with appropriate programming. Accordingly, the invention is limited only by the following claims and equivalents thereto.

What is claimed is:

1. A method of operating an implantable cardiac stimulator to perform cardioverting, the cardiac stimulator having output means for delivering electrical stimulation of a predetermined polarity, amplitude, shape and duration, the method comprising:
   sensing the onset of tachycardia;
   applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:
      a first stimulation phase with a first phase polarity, a first phase amplitude, a first phase shape and a first phase duration; and
      a second stimulation phase with a second phase polarity, a second phase amplitude, a second phase shape and a second phase duration; and
   determining whether pacing capture has occurred;
   wherein in the event it is determined that capture has occurred, the method further comprising:
      continuing biphasic stimulation for a predetermined period of time.

2. The method of operating an implantable cardiac stimulator as in claim 1, wherein it is determined that capture has not occurred, further comprising:
   increasing the stimulation intensity level by predefined increments until capture occurs.

3. The method of operating an implantable cardiac stimulator as in claim 1, wherein the first phase polarity is positive.

4. The method of operating an implantable cardiac stimulator as in claim 1, wherein the first phase duration is at least as long as the second phase duration.

5. The method of operating an implantable cardiac stimulator as in claim 1, wherein the first stimulation phase comprises an anodal stimulus.

6. A method of operating an implantable cardiac stimulator to perform cardioverting, the cardiac stimulator having output means for delivering electrical stimulation of a predetermined polarity, amplitude, shape and duration, the method comprising:
   sensing the onset of tachycardia;
   applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:
      a first stimulation phase with a first phase polarity, a first phase amplitude, a first phase shape and a first phase duration; and
      a second stimulation phase with a second phase polarity, a second phase amplitude, a second phase shape and a second phase duration; and
   determining whether pacing capture has occurred;
   wherein the first phase amplitude is less than the second phase amplitude.

7. A method of operating an implantable cardiac stimulator to perform cardioverting, the cardiac stimulator having output means for delivering electrical stimulation of a predetermined polarity, amplitude, shape and duration, the method comprising:
   sensing the onset of tachycardia;
   applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:
      a first stimulation phase with a first phase polarity, a first phase amplitude, a first phase shape and a first phase duration; and
      a second stimulation phase with a second phase polarity, a second phase amplitude, a second phase shape
   and a second phase duration; and determining whether pacing capture has occurred;
   wherein the first phase amplitude is ramped from a baseline value to a second value.

8. The method of operating an implantable cardiac stimulator as in claim 7, wherein the second value is equal to the second phase amplitude.

9. The method of operating an implantable cardiac stimulator as in claim 7, wherein the second value is at a maximum subthreshold amplitude.

10. The method of operating an implantable cardiac stimulator as in claim 9, wherein the maximum subthreshold amplitude is about 0.5 to 3.5 volts.

11. The method of operating an implantable cardiac stimulator as in claim 7, wherein the first phase duration is at least as long as the second phase duration.

12. The method of operating an implantable cardiac stimulator as in claim 7, wherein the first phase duration is about one to nine milliseconds.

13. The method of operating an implantable cardiac stimulator as in claim 7, wherein the second phase amplitude is about two volts to twenty volts.

14. The method of operating an implantable cardiac stimulator as in claim 7, wherein the second phase duration is about 0.2. to 0.9 milliseconds.

15. The method of operating an implantable cardiac stimulator as in claim 7, wherein the second phase duration is less than 0.3 milliseconds and the second phase amplitude is greater than 20 volts.

16. A method of operating an implantable cardiac stimulator to perform cardioverting, the cardiac stimulator having output means for delivering electrical stimulation of a predetermined polarity, amplitude, shape and duration, the method comprising:

sensing the onset of tachycardia;

applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and determining whether pacing capture has occurred;

wherein the first stimulation phase further comprises a series of stimulating pulses of a predetermined amplitude, polarity and duration.

17. The operating an implantable cardiac stimulator as in claim 16, wherein the first stimulation phase further comprises a series of rest periods.

18. The method of operating an implantable cardiac stimulator as in claim 17, wherein applying the first stimulation phase further comprises applying a rest period of a baseline amplitude after at least one stimulating pulse.

19. The method of operating an implantable cardiac stimulator as in claim 18, wherein the rest period is of equal duration to the duration of the stimulating pulse.

20. A method of operating an implantable cardioverter-defibrillator (ICD), the ICD having output means for delivering electrical stimulation of a predetermined polarity, amplitude, shape and duration, the method comprising:

sensing the onset of arrhythmia;

applying biphasic stimulation at a first intensity level selected from the group consisting of at the diastolic depolarization threshold, below the diastolic depolarization threshold or above the diastolic depolarization threshold wherein biphasic stimulation comprises:

a first stimulation phase with a first phase polarity, a first phase amplitude, a first phase shape and a first phase duration, and a second stimulation phase with a second phase polarity, a second phase amplitude, a second phase shape and a second phase duration; and determining whether capture has occurred;

wherein the first phase amplitude is ramped from a baseline value to a second value;

wherein the first stimulation phase further comprises:

a series of stimulating pulses of a predetermined amplitude, polarity and duration; and a series of rest periods;

wherein applying the first stimulation phase further comprises applying a rest period of a baseline amplitude after at least one stimulating pulse; and wherein the rest period is of equal duration to the duration of the stimulating pulse.

21. The method of operating an ICD as in claim 20, wherein the first stimulation phase comprises an anodal stimulus.

22. A method of operating an implantable cardiac stimulator to perform cardioverting, the cardiac stimulator having output means for delivering electrical stimulation of a predetermined polarity, amplitude, shape and duration, the method comprising:

sensing the onset of tachycardia;

applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and determining whether pacing capture has occurred;

wherein the first phase amplitude is at a maximum subthreshold amplitude.

23. The method of operating an implantable cardiac stimulator as in claim 22, wherein the maximum subthreshold amplitude is about 0.5 to 3.5 volts.

24. A method of operating an implantable cardiac stimulator to perform cardioverting, the cardiac stimulator having output means for delivering electrical stimulation of a predetermined polarity, amplitude, shape and duration, the method comprising:

sensing the onset of tachycardia;

applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and determining whether pacing capture has occurred;

wherein the first phase duration is about one to nine milliseconds.

25. A method of operating an implantable cardiac stimulator to perform cardioverting, the cardiac stimulator having output means for delivering electrical stimulation of a predetermined polarity, amplitude, shape and duration, the method comprising:

sensing the onset of tachycardia;

applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and determining whether pacing capture has occurred;

wherein the second phase duration is about 0.2 to 0.9 milliseconds.

26. A method of operating an implantable cardiac stimulator to perform cardioverting, the cardiac stimulator having output means for delivering electrical stimulation of a predetermined polarity, amplitude, shape and duration, the method comprising:

sensing the onset of tachycardia;
applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:
  a first stimulation phase with a first phase polarity, a first phase amplitude, a first phase shape and a first phase duration; and
  a second stimulation phase with a second phase polarity, a second phase amplitude, a second phase shape and a second phase duration; and
determining whether pacing capture has occurred;
wherein the second phase amplitude is about two volts to twenty volts.

27. A method of operating an implantable cardiac stimulator to perform cardioverting, the cardiac stimulator having output means for delivering electrical stimulation of a predetermined polarity, amplitude, shape and duration, the method comprising:
sensing the onset of tachycardia;
applying pulses of biphasic pacing stimulation at a first intensity level selected from the group consisting of at the diastolic depolarization threshold, below the diastolic depolarization threshold or above the diastolic depolarization threshold, wherein each pulse of biphasic pacing stimulation comprises:
  a first stimulation phase with a first phase polarity, a first phase amplitude, a first phase shape and a first phase duration; and
  a second stimulation phase with a second phase polarity, a second phase amplitude, a second phase shape and a second phase duration; and
determining whether pacing capture has occurred;
wherein the second phase duration is less than 0.3 milliseconds and the second phase amplitude is greater than 20 volts.

28. A method of operating an implatable cardioverter-defibrillator (ICD), the ICD having output means for delivering electrical stimulation of a predetermined polarity, amplitude, shape and duration, the method comprising:
sensing the onset of arrhythmia;
applying biphasic stimulation at a first intensity level selected from the group consisting of at the diastolic depolarization threshold, below the diastolic depolarization threshold or above the diastolic depolarization threshold wherein biphasic stimulation comprises:
  a first stimulation phase with a first phase polarity, a first phase amplitude, a first phase shape and a first phase duration, and
  a second stimulation phase with a second phase polarity, a second phase amplitude, a second phase shape and a second phase duration; and
determining whether capture has occurred;
wherein the first phase amplitude is ramped from a baseline value to a second value; and
wherein the second phase duration is about 0.2 to 0.9 milliseconds.

29. The method of operating an ICD as in claim 28, wherein the first stimulation phase comprises an anodal stimulus.

30. A method of operating an implantable cardioverter-defibrillator (ICD), the ICD having output means for delivering electrical stimulation of a predetermined polarity, amplitude, shape and duration, the method comprising:
sensing the onset of arrhythmia;
applying biphasic stimulation at a first intensity level selected from the group consisting of at the diastolic depolarization threshold, below the diastolic depolarization threshold or above the diastolic depolarization threshold wherein biphasic stimulation comprises:
  a first stimulation phase with a first phase polarity, a first phase amplitude, a first phase shape and a first phase duration, and
  a second stimulation phase with a second phase polarity, a second phase amplitude, a second phase shape and a second phase duration; and
determining whether capture has occurred;
wherein the first phase amplitude is ramped from a baseline value to a second value; and
wherein the second phase duration is less than 0.3 milliseconds and the second phase amplitude is greater than 20 volts.

31. The method of operating an ICD as in claim 30, wherein the first stimulation phase comprises an anodal stimulus.

32. A method of operating an implantable cardioverter-defibrillator (ICD), the ICD having output means for delivering electrical stimulation of a predetermined polarity, amplitude, shape and duration, the method comprising:
sensing the onset of arrhythmia;
applying biphasic stimulation at a first intensity level selected from the group consisting of at the diastolic depolarization threshold, below the diastolic depolarization threshold or above the diastolic depolarization threshold wherein biphasic stimulation comprises:
  a first stimulation phase with a first phase polarity, a first phase amplitude, a first phase shape and a first phase duration, and
  a second stimulation phase with a second phase polarity, a second phase amplitude, a second phase shape and a second phase duration; and
determining whether capture has occurred;
wherein the first stimulation phase is initiated greater than 200 milliseconds after completion of a cardiac beating cycle.

33. The method of operating an ICD as in claim 32, wherein the first stimulation phase comprises an anodal stimulus.

34. A method of operating an implantable cardioverter-defibrillator )ICD), the ICD having output means for delivering electrical stimulation of a predetermined polarity, amplitude, shape and duration, the method comprising:
sensing the onset of arrhythmia;
applying stimulation selected from the group consisting of biphasic stimulation and conventional stimulation at a first intensity level selected from the group consisting of at the diastolic depolarization threshold, below the diastolic depolarization threshold or above the diastolic depolarization threshold;
determining whether capture has occurred;
increasing the stimulation intensity level by predefined increments until capture does occurs; and upon capture,
continuing stimulation selected from the group consisting of biphasic stimulation and conventional stimulation at a second intensity level below the diastolic depolarization threshold.

35. A method of operating an implantable cardioverter-defibrillator (ICD), the ICD having output means for delivering electrical stimulation of a predetermined polarity, amplitude, shape and duration, the method comprising:

defining a first stimulation phase with a positive polarity, a first phase amplitude, a first phase shape and a first phase duration, wherein said first phase amplitude is about 0.5 to 3.5 volts, wherein said first phase duration is about one to nine milliseconds and wherein said first stimulation phase is initiated greater than 200 milliseconds after completion of a cardiac beating cycle;

defining a second phase with a negative polarity, a second phase amplitude, a second phase shape and a second phase duration, wherein said second phase amplitude is about four volts to twenty volts and wherein said second phase duration is about 0.2 to 0.9 milliseconds; and sensing the onset of arrhythmia;

applying the first stimulation phase and the second stimulation phase in sequence to the cardiac tissue;

determining whether capture has occurred; and increasing the stimulation intensity level by predefined increments until capture occurs.

36. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:
a first stimulation phase with a first phase polarity, a first phase amplitude, a first phase shape and a first phase duration; and
a second stimulation phase with a second phase polarity, a second phase amplitude, a second phase shape and a second phase duration; and wherein in the event that the means for determining determines that capture has occurred, the output means continues biphasic stimulation for a predetermined period of time.

37. The cardiac stimulator as in claim 36, wherein in the event that the means for determining determines that capture has not occurred, the output means increases the stimulation intensity level by predefined increments until capture occurs.

38. The cardiac stimulator as in claim 36, wherein the first stimulation phase comprises an anodal stimulus.

39. The cardiac stimulator as in claim 36, wherein the first phase duration is at least as long as the second phase duration.

40. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:
a first stimulation phase with a first phase polarity, a first phase amplitude, a first phase shape and a first phase duration; and
a second stimulation phase with a second phase polarity, a second phase amplitude, a second phase shape and a second phase duration; and wherein the first phase amplitude is less than the second phase amplitude.

41. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:
a first stimulation phase with a first phase polarity, a first phase amplitude, a first phase shape and a first phase duration; and
a second stimulation phase with a second phase polarity, a second phase amplitude, a second phase shape and a second phase duration; and wherein the first phase amplitude is ramped from a baseline value to a second value.

42. The cardiac stimulator as in claim 41, wherein the second value is equal to the second phase amplitude.

43. The cardiac stimulator as in claim 41, wherein the second value is at a maximum subthreshold amplitude.

44. The cardiac stimulator as in claim 43, wherein the maximum subthreshold amplitude is about 0.5 to 3.5 volts.

45. The cardiac stimulator as in claim 41, wherein the first phase duration is at least as long as the second phase duration.

46. The cardiac stimulator as in claim 44, wherein the first phase duration is about one to nine milliseconds.

47. The cardiac stimulator as in claim 44, wherein the second phase duration is about 0.2 to 0.9 milliseconds.

48. The cardiac stimulator as in claim 41, wherein the second phase amplitude is about two volts to twenty volts.

49. The cardiac stimulator as in claim 41, wherein the second phase duration is less than 0.3 milliseconds and the second phase amplitude is greater than 20 volts.

50. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:
a first stimulation phase with a first phase polarity, a first phase amplitude, a first phase shape and a first phase duration; and a second stimulation phase with a second phase polarity, a second phase amplitude, a second phase shape and a second phase duration; and wherein the first stimulation phase further comprises a series of stimulating pulses of a predetermined amplitude, polarity and duration.

51. The cardiac stimulator as in claim 50, wherein the first stimulation phase further comprises a series of rest periods.

52. The cardiac stimulator as in claim 51, wherein applying the first stimulation phase further comprises applying a rest period of a baseline amplitude after at least one stimulating pulse.

53. The cardiac stimulator as in claim 52, wherein the rest period is of equal duration to the duration of the stimulating pulse.

54. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and wherein the first phase amplitude is at a maximum subthreshold amplitude.

55. The cardiac stimulator as in claim 54, wherein the maximum subthreshold amplitude is about 0.5 to 3.5 volts.

56. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and wherein the first phase duration is about one to nine milliseconds.

57. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and wherein the second phase duration is about 0.2 to 0.9 milliseconds.

58. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and wherein the second phase amplitude is about two volts to twenty volts.

59. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and wherein the second phase duration is less than 0.3 milliseconds and the second phase amplitude is greater than 20 volts.

60. A cardiac stimulator to perform cardioverting, the cardiac stimulator comprising:

sensing means for sensing the onset of tachycardia;

output means for delivering, in response to the sensing means, electrical stimulation of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and means for determining whether capture has occurred;

wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and wherein the first stimulation phase is initiated greater than 200 milliseconds after completion of a cardiac beating cycle.

61. An implantable cardiac stimulator device comprising:

plural electrodes;

sensing circuitry connected to the plural electrodes and adapted to sense the onset of tachycardia;

detecting circuitry connected to the sensing circuitry and adapted to detect whether pacing capture has occurred; and pulse generating circuitry connected to the plural electrodes and adapted to generate, in response to the sensing circuitry, electrical pulses of a predetermined polarity, amplitude, shape and duration to cause application of pulses of biphasic pacing stimulation at a first intensity level selected from the group consisting of: at the diastolic depolarization threshold, below the diastolic depolarization threshold, and above the diastolic depolarization threshold; and wherein each pulse of biphasic pacing stimulation comprises:

a first stimulation phase with a first phase polarity, a first phase amplitude, a first phase shape and a first phase duration; and a second stimulation phase with a second phase polarity, a second phase amplitude, a second phase shape and a second phase duration; and wherein, in the event that the detecting circuitry determines that capture has occurred, the pulse generating circuitry continues biphasic stimulation for a predetermined period of time.

62. The implantable cardiac stimulator device as in claim 61, wherein, in the event that the detecting circuitry determines that capture has not occurred, the pulse generating circuitry increases the stimulation intensity level by predefined increments until capture occurs.

* * * * *